(12) United States Patent
Strobel

(10) Patent No.: US 10,485,754 B2
(45) Date of Patent: Nov. 26, 2019

(54) METHOD FOR THE PRODUCTION OF A SODIUM ION-FREE EFFERVESCENT TABLET, POWDER OR GRANULATE HAVING A HIGH X ION CONTENT, WHERE X CAN BE A VARIETY OF SUBSTANCES

(71) Applicant: BIOFAR LABORATOIRES, Nanterre (FR)

(72) Inventor: Hanspeter Strobel, Davos-Platz (CH)

(73) Assignee: BIOFAR LABORATORIES, Nanterre (FR)

( * ) Notice: Subject to any disclaimer, the term of this patent is extended or adjusted under 35 U.S.C. 154(b) by 0 days.

(21) Appl. No.: 15/526,457

(22) PCT Filed: Nov. 12, 2015

(86) PCT No.: PCT/IB2015/058756
§ 371 (c)(1),
(2) Date: May 12, 2017

(87) PCT Pub. No.: WO2016/075655
PCT Pub. Date: May 19, 2016

(65) Prior Publication Data
US 2017/0319471 A1 Nov. 9, 2017

(30) Foreign Application Priority Data
Nov. 12, 2014 (CH) ........................ 1758/14

(51) Int. Cl.
*A61K 9/46* (2006.01)
*A61K 33/10* (2006.01)
*A23L 33/16* (2016.01)
*A23L 2/40* (2006.01)

(52) U.S. Cl.
CPC .............. *A61K 9/0007* (2013.01); *A23L 2/40* (2013.01); *A23L 33/16* (2016.08); *A61K 33/10* (2013.01); *A23V 2002/00* (2013.01)

(58) Field of Classification Search
CPC .......... A23L 2/40; A61K 33/10; A61K 9/0007
See application file for complete search history.

(56) References Cited

U.S. PATENT DOCUMENTS

| 4,678,661 A * | 7/1987 | Gergely | .................... A23L 2/40 |
| | | | 424/44 |
| 5,707,654 A | 1/1998 | Beres | |
| 7,781,002 B2 * | 8/2010 | Baldwin | ............... A23L 33/165 |
| | | | 426/648 |

FOREIGN PATENT DOCUMENTS

| CH | 662926 A5 | 11/1987 | |
| DE | 69416115 T2 | 9/1999 | |
| EP | 0076340 A1 | 4/1983 | |
| EP | 0948961 A2 * | 3/1999 | ........... A61K 9/0007 |
| EP | 1452097 A | 9/2004 | |
| WO | WO/1995/007070 A1 | 3/1995 | |

OTHER PUBLICATIONS

International Search Report of PCT/IB2015/058756 and English translation, the whole document.
Written Opinion of PCT/IB2015/058756 by ISA and English translation, the whole document.

* cited by examiner

*Primary Examiner* — Gina C Justice
(74) *Attorney, Agent, or Firm* — CUSPA Technology Law Associates, P.A.

(57) ABSTRACT

The process serves for preparing sodium ion-free X carbonate or hydrogencarbonate effervescent powder, such granules or such tablets. The active substances X, at least calcium carbonate, moistened with a small amount of alcohol and water, are mixed as powder with a small amount of lactobionic acid in a partial vacuum in a vacuum tank with continual pumping. As a result, the calcium salt ($CaCO_3$) of the calcium in the surface layer of the powder particles reacts with the lactobionic acid, effervesces and releases a small amount of $CO_2$. Consequently, the pressure in the vacuum tank rises and after the end of the effervescent reaction the internal pressure in the vacuum tank drops back to the starting value through the continual pumping. In so doing, the powder dries. After removal from the vacuum chamber an acid, preferably citric acid, as an effervescing agent is added, and subsequently the powder is electively pressed into tablets. The thus produced sodium ion-free calcium carbonate effervescent tablet hence contains at least calcium carbonate as well as citric acid as an effervescing agent, with the pressed particles having been initially effervesced in their surface layer by means of lactobionic acid.

7 Claims, No Drawings

METHOD FOR THE PRODUCTION OF A SODIUM ION-FREE EFFERVESCENT TABLET, POWDER OR GRANULATE HAVING A HIGH X ION CONTENT, WHERE X CAN BE A VARIETY OF SUBSTANCES

This invention relates to a process for preparing a sodium ion-free effervescent tablet or such a powder or granules as a supplier of, electively, calcium, magnesium, potassium or a mixture of said substances, wherein said effervescent tablet or powder or granules are to be soluble in water quickly and completely.

Food products manufactured for general consumption are often modified by added nutrients or other kinds of additives in order to improve their nutrient properties. Nutrient fortification of food products can involve additives that are conducive to the overall state of health of the human body. Examples of nutrient fortification are the addition of vitamins, minerals and comparable materials. Such additives are either absolutely essential to the human metabolism or they promote the supply of substances that are not available in sufficient quantities in a normal diet.

In the recent past, calcium fortification of food and beverages has gained considerable attention. According to reports, calcium fortification and increased calcium intake are especially useful for preventing or alleviating the effects of osteoporosis. Increased dietary calcium intake has proved effective for minimizing bone loss in adults and older persons. Moreover, increased calcium consumption in younger years can create reserves that enable greater tolerance in case of a negative calcium balance in later years. Increased calcium consumption is said to moderate or delay the effects of osteoporosis regardless of age. Hence, persons of any age might benefit from increased calcium consumption. Unfortunately, many of the persons with the greatest need for calcium, including children, women and older people, do not consume the recommended daily amounts of calcium. According to United States Department of Agriculture surveys, for example, nine out of ten women in the U.S. do not consume the recommended amounts of calcium. Older people often have difficulties increasing their calcium consumption due to decreasing appetite and metabolism. Besides bone health, the latest research points out the importance of calcium for improving colon health, weight control and other health criteria. The daily value currently recommended by experts as ideal for the supply of calcium lies at 1000 mg per day.

Such calcium supplements have been used in a great number of food products. U.S. Pat. No. 4,784,871 (15 Nov. 1988) provides e.g. a calcium-fortified yogurt. According to the patent, any acid-soluble calcium compound might be employed. U.S. Pat. No. 5,449,523 (12 Sep. 1995) and U.S. Pat. No. 5,820,903 (13 Oct. 1998) likewise provide calcium-enriched yogurts. U.S. Pat. No. 5,478,587 (27 Dec. 1995) states calcium-enriched desserts.

U.S. Pat. No. 5,834,045 (10 Nov. 1998) states calcium-fortified acidic beverages. This patent reports that the use of a calcium source containing calcium hydroxide and calcium glycerophosphate yields, with an acidulant, a beverage product having distinctly improved storage stability. U.S. Pat. No. 5,855,936 (5 Jan. 1999) describes a mixture of calcium salts balanced with soluble and insoluble salts which are stabilized with a glucuronic acid source. This composition can fortify milk beverages and other dairy products without coagulation and sedimentation and with improved palatability. The calcium salts must be stabilized with the glucuronic acid source. Other calcium sources might electively be contained. Other calcium-enriched beverages are described e.g. in U.S. Pat. No. 4,642,238 (10 Feb. 1987, dietary and nutritionally balanced beverages); U.S. Pat. No. 4,701,329 (20 Oct. 1987, milk); U.S. Pat. No. 4,737,375 (12 Apr. 1988, carbonated and non-carbonated beverages with solubilized calcium and specific quantities).

Conventionally, there are also effervescent tablets for supplying calcium as a supplementary additive for the needs of the human body or animal body. Such effervescent calcium tablets have been known for many decades, but they always resort to sodium ion (HST) to ensure solubility in water. Sodium has the negative effect of increasing blood pressure because it retains water in the blood, which can be critical particularly in older persons with slower digestion and increases the risk of stroke or thrombosis. Hence, the effervescent tablets should best not contain any sodium ion or sodium.

Such effervescent calcium ion tablets $CaCO_3$ are administered in case of calcium deficiency and vitamin D deficiency or also used to combat and dissolve urinary stones, such as kidney stones, bladder stones or ureteral stones, that is, deposits of urinary salts. The citrates contained in Blemaren alkalize the urine, that is, they increase the pH value of the urine. This can cause stones to be dissolved, or their growth hindered.

A typical composition of such an effervescent tablet contains for example, with respect to calcium and sodium ion:

| | |
|---|---|
| Calcium carbonate | 2000 mg |
| Calcium ion | 800 mg |
| Sodium hydrogencarbonate | 520 mg |
| Sodium ion (HST) | 145 mg |
| Citric acid | 3700 mg |
| Cholecalciferol | 0.02 mg |
| corresponding to | 800 I.U. (International Units) |
| as well as further ingredients, with a total weight of 6500 mg. | |

The object of this invention, against this background, is to show a process for preparing an X ion effervescent tablet or such a powder or granules doing without sodium and nevertheless being soluble in water quickly and completely through effervescence, and to state the constituents of the effervescent tablet or powder that are necessary therefor. As X there is to be used in particular calcium for preparing calcium ion effervescent tablets ($CaCO_3$), but the process is also to be implementable with magnesium or potassium or a mixture of said substances instead of calcium or X.

This object is achieved by a process for preparing a sodium ion-free X carbonate or hydrogencarbonate effervescent powder or such granules or such a tablet, wherein the active substances, corresponding at least to calcium carbonate, magnesium carbonate, magnesium hydrogencarbonate, potassium carbonate, potassium hydrogencarbonate, or mixtures thereof, moistened with a small amount of alcohol and water, are mixed as powder with a small amount of lactobionic acid in a partial vacuum in a vacuum tank with continual pumping, by which the surface layer of the powder particles reacts with the lactobionic acid, effervesces, and releases a small amount of $CO2$, by which the pressure in the vacuum chamber rises, and after the end of the effervescent reaction the pressure in the partial vacuum drops back to the starting value through the continual pumping and in so doing the powder dries, and after removal from the vacuum chamber an acid as an effervescing agent for effervescing is added to said powder, and the latter is subsequently usable as effervescent powder or pressed into tablets.

Further, the object is achieved by a sodium ion-free effervescent tablet or such a powder or granules, prepared by said process, as characterized by the features of claim 5, that the sodium ion-free X carbonate or hydrogencarbonate effervescent powder or such granules or such a tablet contains at least an X carbonate as well as an acid as an effervescing agent, and wherein the pressable powder particles or the particles pressed into an effervescent tablet are initially effervesced in their surface layer by means of lactobionic acid.

An example of a composition of an effervescent tablet with calcium carbonate as the main constituent is the following composition:

| | |
|---|---|
| Calcium carbonate | 2000 mg |
| Potassium hydrogencarbonate | 550 mg |
| Lactobionic acid | 480 mg |
| Citric acid | 3200 mg |
| Cholecalciferol | 0.02 mg |
| corresponding to | 800 I.U. (International Units) |

Calcium carbonate is actually nothing but marble that is present as very fine powder. And such powder is practically insoluble in water, that is, only 0.014 grams of calcium carbonate can be dissolved in one liter of water. With $CO_2$ soda in the water, however, up to 16.6 grams of calcium carbonate can be dissolved in one liter of water. It is hence necessary to first generate the gas $CO_2$ in the water. And exactly this can be excellently done using for example potassium hydrogencarbonate, because in small amounts potassium hydrogencarbonate is considered a food additive and can hence be employed without hesitation for this purpose. For 3000 mg of calcium carbonate (with magnesium carbonate, magnesium hydrogencarbonate, potassium carbonate and potassium hydrogencarbonate each alone or mixtures thereof with calcium carbonate also producing the same effects) 550 mg of potassium hydrogencarbonate suffices, which is brought to effervescence with lactobionic acid and thus to generate $CO_2$. The resulting $CO_2$ then in turn causes a decisive improvement in the water solubility of the calcium carbonate, namely, up to 16.6 grams per liter of water. At the same time, the lactobionate ion also ensures a better solubility of the calcium ions. Potassium hydrogencarbonate is used in principle in interaction with the lactobionic acid as a starter for the solubility process for the calcium carbonate.

Further, the initial effervescing of the calcium carbonate powder particles by means of lactobionic acid causes an irregular decomposition of their surface layer, by individual calcium ions reacting with the lactobionic acid and releasing $CO_2$ there. This makes the surfaces of the particles porous and rough. Then the powder previously moistened with alcohol and water (=granulating liquid) is dried out in a partial vacuum. This process can be repeated if necessary in order to effect an intimate initial effervescing. The thus pre-prepared powder is mixed with an acid as an effervescing agent, preferably with citric acid, and subsequently pressed into tablets. Instead of citric acid there can also be used malic acid, succinic acid, fumaric acid, tartaric acid or ascorbic acid, or mixtures of all said acids.

The thus produced calcium ion effervescent tablets ($CaCO_3$) serve for mineral fortification of food and beverage products. They form a stable, pure-tasting calcium source which is suitable for calcium fortification of a great variety of food and beverage products. When calcium is replaced by other substances, such as magnesium or potassium or also mixtures of all said substances, further supplements are accordingly made available to the body.

Lactobionic acid is generally a white crystalline powder. Lactobionic acid may be obtained commercially or prepared through chemical or enzymatic oxidation of lactose or a lactose-containing substrate. The lactobionic acid can be prepared by chemical saccharide oxidation or bioconversion processes (for example, catalytic action of a carbohydrate oxidase enzyme) using lactose or a lactose-containing substrate (for example, whey or whey permeate) as the starting material. In principle, lactobionic acid is a by-product of the dairy industry. Suitable carbohydrate oxidase enzymes are for example lactose oxidase, glucose oxidase, hexose oxidase, and the like, as well as mixtures thereof. Generally, lactose oxidase is preferred. An especially suitable enzyme for lactose oxidation has been developed by Novozymes NS and is described in WO 99/31990.

The process according to the invention allows the preparation of effervescent tablets or effervescent granules that not only possess excellent storage stability but are also always constant in their quality since the reproducibility of the process is guaranteed at all times through the control of a number of reaction parameters. The process for preparing effervescent tablets or processable effervescent granules is effected through heat treatment at 30° C. to 100° C. from acid and hydrogencarbonate and/or carbonate together with the granulating liquid as the essential effervescent constituents. The powdery or grainy mixture is treated in a closed system in a partial vacuum, wherein the acid (a dosed amount of up to 7% by mass, based on the mass of the mixture, of lactobionic acid) is mixed with the necessary quantity of hydrogencarbonate and/or carbonate, and this mixture is thereupon mixed with a polar solvent such as water, alcohol, methanol, or mixtures thereof, and granulated. The vacuum treatment at a temperature of 30° C. to 100° C., preferably 40° C. to 80° C., leads to roughening of the surface layer of at least one of the reaction components or to conversion thereof to a dry state with faster solubility. A $CO_2$ evolution arising therefrom due to the reaction that occurs causes the pressure in the vacuum tank to initially rise, up to a maximum of 1000 mbar (atmospheric pressure). From the pressure difference relative to the starting value of for example 10 mbar in the vacuum tank one can establish the volume and the mass of the released $CO_2$. The heat treatment after the fast vacuum drying of the mixture in each case can be repeated until the distinct slowing-down of the reaction or decreased gas evolution indicates the end of the surface roughening.

The obtained aggregates are thereupon reduced to a desired particle size, furnished with the desired additives, where applicable, and then tableted into effervescent tablets by means of a tablet press.

The temperature at which the process according to the invention is carried out is not critical and best lies between 40 and 80° C. The negative pressure that is used should be as low as possible. Thus, the starting partial vacuum can have a pressure of for example 10 mbar. The polar solvent is preferably water, which is used in a quantity of 0.2 to 2% by mass, based on the weight of the mixture to be treated.

Carrying out the process according to the invention has shown that when using suitable concentrations of the reactants and suitable quantities of polar solvent only a portion of the reactants reacts, and that soon, after 10-20 minutes have passed, the reaction becomes distinctly slower. When the mixture that has been thus reacted and slowly stirred further is now abruptly dried, then this operation can be repeated under suitable conditions, it turning out upon repetition that the stated operation is slowed down because a large portion of the surface of the acid has already been passivated and made inert by alkali or alkaline earth salts. When the same reaction is now carried out a third time, then one can ascertain that almost no more reaction takes place, since the total surface is already passivated and the individual reactants are inherently buffered. There has thus arisen an inert mixture which no longer, or only very slowly, reacts even in contact with small quantities of polar solvents. It is obvious that the prepared mixtures in the dry state have very high stability even at higher temperatures, so that the entry of air moisture or a long storage at higher temperatures cannot bring about any further reactions.

Since according to the invention the released quantity of $CO_2$ is ascertained, one can establish by way of simple stoichiometric calculations how much bicarbonate has been consumed or how much salt has been formed with the lactobionic acid. One is now readily able to determine, through suitable parameters such as for instance the stirring rate, the applied amount of moisture from e.g. water and alcohol, the grain size of the applied lactobionic acid, how much lactobionic acid reacts to acid salt on the surface thereof.

For example, if 40 kg of a reaction mixture is reacted in a closed 100 liter vessel, then the free space between mass and tank capacity will amount to about 50 liters depending on the bulk weight of the mass. If the vessel was evacuated before the reaction, then these 50 liters of free space will be practically gas-free. If a quantitatively determined amount of moisture is now made to flow into the mass with simultaneous stirring, then the corresponding carbon dioxide will fill the supernatant space of 50 liters. This filling of the space can be easily checked with a good manometer. Thus, if the initial partial vacuum was 10 mbar and the reaction has caused the pressure in the vacuum tank to rise to for example atmospheric pressure, then that means that about 50 liters of carbon dioxide have been produced.

It can now be calculated back how much lactobionic acid has in this case been consumed or how much lactobionate or how much citrate produced. Multiple repetition of the described vacuum treatment leads almost to a standstill of the reaction between the reactants, i.e. the lactobionic acid and the calcium salt of the calcium.

Even in the presence of polar solvents and despite the small quantities of reacted materials, hardly any reaction can be ascertained any more, so that after final drying of the product an exceptionally resistant but still reactive mass is obtained. The results are moreover strictly reproducible if the above-mentioned parameters are kept the same and guarantee the recovery of a product of unvarying quality.

As a theoretical explanation for the effect achieved by the process according to the invention it may be put forward that the contact areas of the reactants form buffer zones that are formed by different alkaline or alkaline earth salts of the corresponding acid. Said buffer zones will of course form depending on the surface of the individual crystals and on the reactivity.

Hereinafter an example with numbers will be given: In a 100 liter vacuum tank 29 kg of citric acid and 1 kg to 3 kg of lactobionic acid are provided and heated while stirring to 60° C. for 5 min, after which evacuation is briefly effected to 20 mbar in the vacuum tank for checking the residual moisture. After the vacuum is broken 10 kg of calcium carbonate is added, whereupon heating to 60° C. is again effected with further stirring. This mixture with the lactobionic acid then has a bulk weight per volume of approximately 1250 kg/m$^3$, so that the space remaining in the vacuum tank amounts to about 50 liters. Then the tank is evacuated to 10 mbar, blocked off from the pump by means of a valve, and a quantity of 210 ml of water is introduced while stirring. Upon the now commencing reaction between the lactobionic acid and the hydrogencarbonate so as to form a passivating surface layer on the acid crystals and evolving $CO_2$, the pressure in the vacuum tank rises from 10 mbar to 1000 mbar, which corresponds to a volume of released $CO_2$ of 50 liters or, at a molar volume of the $CO_2$ at 60° C. of 27.1 liters, to a mass of released $CO_2$ of 81 grams.

From this it results that upon this first vacuum treatment a portion of the lactobionic acid reacted with the surface layer of the particles, that is, of the calcium salt of the calcium, and released $CO_2$. The reaction time amounts to approx. 4 min. Now the treated product is dried and vacuum-treated, repeated under the same conditions and using 300 ml of water. In so doing, the pressure in the vacuum tank is made to rise to 1000 mbar again, corresponding to a volume of 50 liters or a mass of 81 grams of $CO_2$. Due to the partial initial effervescence of the surface layer through the lactobionic acid achieved in the first treatment, the reaction time is substantially longer this time and amounts to about 10 to 30 minutes. The treated product is dried again and subjected to a third vacuum treatment, with only an insignificant pressure increase being measured because the lactobionic acid is used up, so that substantially no more $CO_2$ generation takes place. The surface of the acid crystals is largely initially effervesced or has been passivated, that is, no further reaction takes place. The product is then dried and the obtained agglomerates can be reduced to the desired particle size and can be mixed with the desired additives such as flavoring materials, vitamins, sweeteners and the like. For later effervescing, an acid is added in the conventional way, preferably citric acid, but other acids such as malic acid, succinic acid, fumaric acid, tartaric acid or ascorbic acid, as well as mixtures of said acids, also work. These effervescent granules can be pressed into effervescent tablets by means of tablet presses in the known manner, where applicable.

The thus obtained product has excellent storage stability for long time periods even at tropical temperatures. The described pretreatment by means of lactobionic acid accelerates effervescing and makes it deep-acting because all the powder particles have been "initially effervesced", that is, they offer a far greater surface for the later reaction with the admixed acid, for example citric acid, as soon as the effervescent tablet comes in contact with water.

When a thus prepared effervescent tablet is placed in water at ambient temperature, the water quickly penetrates into the surface layer of the powder particles and leads to an effervescent effect which effervesces the whole effervescent tablet quickly progressing toward the interior and dissolves it completely in water. After less than three minutes the effervescent tablet is completely dissolved and the solution is even clear.

The invention claimed is:

1. A process for preparing sodium ion-free X carbonate or hydrogencarbonate effervescent powder, granules, or tablets, wherein at least one active substance of sodium ion-free X carbonate or hydrogencarbonate is moistened with alcohol or water to form powder particles, and the powder particles are mixed with lactobionic acid in a partial vacuum in a vacuum tank with continual pumping, wherein a surface layer of the powder particles reacts with the lactobionic acid, effervesces, and releases $CO_2$ in an initial effervescent reaction, causing pressure in the vacuum tank to rise, and after the initial effervescent reaction the pressure in the vacuum tank drops down through the continual pumping, thereby resulting in vacuum dried, initial effervescent reaction treated powder particles, and wherein after removal from the vacuum tank, an effervescing agent is added to the initial effervescent reaction treated powder particles to form a product of sodium ion-free X carbonate or hydrogencarbonate effervescent powder, granules or tablets.

2. The process according to claim 1, wherein the effervescing agent is one or more of citric acid, malic acid, succinic acid, fumaric acid, tartaric acid, or ascorbic acid.

3. The process according to claim 1, wherein the at least one active substance is potassium hydrogencarbonate and calcium carbonate.

4. The process according to claim 1, wherein the lactobionic acid is added and mixed with the powder particles multiple times in the vacuum tank in a partial vacuum, each time a further effervescent reaction of the powder particles with the lactobionic acid is carried out and the pressure in the vacuum tank rises more slowly until the surface layer of the powder particles is completely passivated, and then vacuum dried and effervescent reaction treated powder particles are removed from the vacuum tank and processed further.

5. The process according to claim 1, wherein in the X carbonate or hydrogencarbonate, the X is calcium, magnesium, potassium, or a mixture thereof.

6. The process according to claim 1, wherein the at least one active substance is calcium carbonate, magnesium carbonate, magnesium hydrogencarbonate, potassium carbonate, potassium hydrogencarbonate, or mixtures thereof.

7. The process according to claim 1, wherein after the initial effervescent reaction the pressure in the vacuum tank drops back to a starting value prior to the initial effervescent reaction.

* * * * *